United States Patent
Jessop et al.

(10) Patent No.: US 11,179,505 B2
(45) Date of Patent: Nov. 23, 2021

(54) METHODS FOR STABILIZING COLLAGEN-CONTAINING TISSUE PRODUCTS AGAINST ENZYMATIC DEGRADATION

(71) Applicant: LifeCell Corporation, Madison, NJ (US)

(72) Inventors: Israel Jessop, Annandale, NJ (US); Ming F. Pomerleau, Califon, NJ (US); Nathaniel Bachrach, Clifton, NJ (US)

(73) Assignee: LifeCell Corporation, Madison, NJ (US)

( * ) Notice: Subject to any disclaimer, the term of this patent is extended or adjusted under 35 U.S.C. 154(b) by 469 days.

(21) Appl. No.: 16/077,143

(22) PCT Filed: Jan. 26, 2017

(86) PCT No.: PCT/US2017/015067
§ 371 (c)(1),
(2) Date: Aug. 10, 2018

(87) PCT Pub. No.: WO2017/139102
PCT Pub. Date: Aug. 17, 2017

(65) Prior Publication Data
US 2019/0255226 A1    Aug. 22, 2019

Related U.S. Application Data

(60) Provisional application No. 62/294,042, filed on Feb. 11, 2016.

(51) Int. Cl.
*A61L 31/00* (2006.01)
*A61L 31/04* (2006.01)
*A61F 2/00* (2006.01)

(52) U.S. Cl.
CPC .......... *A61L 31/044* (2013.01); *A61F 2/0063* (2013.01); *A61L 31/005* (2013.01); *A61F 2002/0068* (2013.01); *A61L 2430/40* (2013.01)

(58) Field of Classification Search
None
See application file for complete search history.

(56) References Cited

U.S. PATENT DOCUMENTS

| | | |
|---|---|---|
| 4,865,602 A | 9/1989 | Smestad et al. |
| 4,978,352 A | 12/1990 | Fedorov et al. |
| 5,336,616 A | 8/1994 | Livesey et al. |
| 5,364,756 A | 11/1994 | Livesey et al. |
| 5,397,353 A | 3/1995 | Oliver et al. |
| 5,772,439 A | 6/1998 | Yamaoka et al. |
| 5,843,084 A | 12/1998 | Hart et al. |
| 6,203,570 B1 | 3/2001 | Baeke |
| 6,706,684 B1 | 3/2004 | Bayon et al. |
| 6,734,018 B2 | 5/2004 | Wolfinbarger, Jr. et al. |
| 8,093,215 B2 | 1/2012 | Frullini |
| 9,636,435 B2 | 5/2017 | Sun et al. |
| 2002/0103542 A1 | 8/2002 | Bilbo |
| 2003/0035843 A1 | 2/2003 | Livesey et al. |
| 2003/0143207 A1 | 7/2003 | Livesey et al. |
| 2003/0229394 A1 | 12/2003 | Ogle et al. |
| 2006/0073592 A1 | 4/2006 | Sun et al. |
| 2006/0099268 A1* | 5/2006 | Chan ............... A61L 27/50 424/488 |
| 2007/0248575 A1 | 10/2007 | Connor et al. |
| 2008/0027542 A1 | 1/2008 | McQuillan et al. |
| 2008/0131473 A1 | 6/2008 | Brown et al. |
| 2008/0195229 A1 | 8/2008 | Quijano et al. |
| 2009/0035289 A1 | 2/2009 | Wagner et al. |
| 2009/0306790 A1 | 12/2009 | Sun |
| 2009/0317469 A1 | 12/2009 | Johnson et al. |
| 2010/0028396 A1 | 2/2010 | Ward et al. |
| 2010/0161054 A1 | 6/2010 | Park et al. |
| 2011/0002996 A1 | 1/2011 | McQuillan et al. |
| 2011/0022171 A1 | 1/2011 | Richter et al. |
| 2012/0010728 A1 | 1/2012 | Sun et al. |
| 2017/0100509 A1 | 4/2017 | Sun et al. |

FOREIGN PATENT DOCUMENTS

| | | |
|---|---|---|
| CN | 103520772 B | 5/2015 |
| EP | 2483332 A1 | 8/2012 |
| FR | 2786400 A1 | 6/2000 |
| GB | 1073243 A | 6/1967 |
| JP | 11-17258 A | 2/1999 |
| JP | 2009-285155 A | 12/2009 |
| JP | 2012-527283 A | 11/2012 |

(Continued)

OTHER PUBLICATIONS

U.S. Appl. No. 13/177,720, filed Jul. 7, 2011, now U.S. Pat. No. 9,636,435, Issued.
U.S. Appl. No. 15/378,447, filed Dec. 14, 2016, 2017-0100509, Published.
Aldahlawi et al., Standard versus accelerated riboflavin-ultraviolet corneal collagen crosslinking: Resistance against enzymatic digestion. J Cataract Refract Surg. Sep. 2015;41(9):1989-96.
Badylak et al., Extracellular matrix as a biological scaffold material: Structure and function. Acta Biomater. Jan. 2009;5(1):1-13.
Bourroul et al., Sterilization of skin allografts by ionizing radiation. Cell Mol Biol (Noisy-le-grand). Nov. 2002;48(7):803-7.

(Continued)

*Primary Examiner* — Jeanette M Lieb
(74) *Attorney, Agent, or Firm* — McCarter & English, LLP; Matthew R. Van Eman

(57) ABSTRACT

Methods for producing crosslinked tissue matrices, crosslinked tissue matrices produced by such methods, as well as tissue products comprising such tissue matrices are disclosed. The methods comprise (1) dehydrating a collagen-containing tissue matrix to form a dehydrated collagen-containing tissue matrix; and (2) irradiating the dehydrated collagen-containing tissue matrix such that at least a portion of the dehydrated collagen-containing tissue matrix is crosslinked.

9 Claims, 2 Drawing Sheets

(56) References Cited

FOREIGN PATENT DOCUMENTS

| | | |
|---|---|---|
| JP | 2013-535240 A | 9/2013 |
| JP | 2014-503552 A | 2/2014 |
| JP | 2015-110537 A | 6/2015 |
| WO | 1996/15818 A1 | 5/1996 |
| WO | 2002/098223 A1 | 12/2002 |
| WO | 2005/009134 A1 | 2/2005 |
| WO | 2009/001293 A1 | 12/2008 |
| WO | 2009/049568 A2 | 4/2009 |
| WO | 2010/133853 A1 | 11/2010 |
| WO | 2011/074208 A1 | 6/2011 |
| WO | 2012/095877 A1 | 7/2012 |
| WO | 2014/089548 A1 | 6/2014 |

OTHER PUBLICATIONS

Brockbank et al., Vitrification: Preservation of Cellular Implants. Topics in Tissue Engineering. N. Ashammakhi (Ed.). Chapter 12, pp. 1-26, (2003).

Ghosh et al., A comparison of methodologies for the preparation of human epidermal-dermal composites. Ann Plast Surg. Oct. 1997;39(4):390-404.

Huang et al., Use of peracetic acid to sterilize human donor skin for production of acellular dermal matrices for clinical use. Wound Repair Regen. May-Jun. 2004;12(3):276-87.

Ksander et al., Reduced capsule formation around soft silicone rubber prostheses coated with solid collagen. Ann Plast Surg. Apr. 1985;14(4):351-60.

Peyman et al., Collagen cross-linking effect on progressive keratoconus in patients younger than 18 years of age: A clinical trial. Adv Biomed Res. Nov. 23, 2015;4:245.

Rigby et al., The Mechanical Properties of Rat Tail Tendon. J Gen Physiol. Nov. 1, 1959;43(2):265-83.

Rijal et al., A versatile 3D tissue matrix scaffold system for tumor modeling and drug screening. Sci Adv. Sep. 13, 2017;3(9):e1700764, 16 pages.

Strattice, Reconstructive Tissue Matrix, Product Offerings. Retrieved online at: http:hcp.stratticetissuematrix.com/en/products#collapse-3, 4 pages, downloaded Jan. 30, 2019.

Sundararaghavan et al., Genipin-induced changes in collagen gels: correlation of mechanical properties to fluorescence. J Biomed Mater Res A. Nov. 2008;87(2):308-20.

Tadafumi, Irradiated SoyAct ingredient problem should be thoroughly investigated. Food Safety Citizen's Watch English Newsletter, Issue 13. Retrieved online at: http://www.fswatch.org/newsletter/english/issue13.html. 2 pages, Dec. 10, 2007.

Yoshinaga et al., Protection by trehalose of DNA from radiation damage. Biosci Biotechnol Biochem. Jan. 1997;61 (1):160-1.

International Search Report and Written Opinion for Application No. PCT/US2017/015067, dated Jun. 30, 2017, 19 pages.

\* cited by examiner

Reduced susceptibility to in vitro collagenase digestion in the riboflavin UVA treated ADM, as demonstrated by the percentage remaining dry weight measured post 6 and 25 hrs collagenase (50 U/ml) digestion.

METHODS FOR STABILIZING COLLAGEN-CONTAINING TISSUE PRODUCTS AGAINST ENZYMATIC DEGRADATION

This application is a 35 U.S.C. § 371 national stage filing of International Application No. PCT/US2017/015067, filed on Jan. 26, 2017, which claims priority to U.S. Provisional Patent Application Ser. No. 62/294,042, filed on Feb. 11, 2016. Each of the foregoing applications are hereby incorporated herein by reference in their entirety.

The present disclosure relates to methods of stabilizing collagen-containing extracellular tissue matrices against enzymatic degradation by crosslinking. The present disclosure also relates to crosslinked collagen-containing extracellular tissue matrices produced by such methods, as well as to tissue products produced from such matrices.

Collagen-containing tissue products are frequently used to regenerate, repair, augment, or otherwise treat diseased or damaged tissues and organs. When implanted in or on a patient or animal, these tissue products are subject to enzymatic degradation over time, disrupting the collagen and/or other proteins and causing a decrease in or change in various mechanical properties (e.g., breaking load, strength, elasticity, suture retention strength, stiffness, etc.) of the tissue product.

Some mechanical properties of collagen-based materials can be increased by the incorporation of intermolecular crosslinks. In addition, cross-linking can reduce the enzymatic susceptibility to some enzymes. Thus, collagen-containing tissue can be stabilized against enzymatic degradation, and the concomitant decrease in mechanical properties, through crosslinking. Collagen can be crosslinked via chemical methods, such as through the use of chemical crosslinkers containing aldehyde, isocyanate, and/or carbodiimide functionalities. However, the use of chemical crosslinkers may raise biocompatibility concerns.

Alternatively, collagen-containing tissue can be crosslinked via irradiation, e.g., with ultraviolet (UV) light. Crosslinking with UV light is rapid and effective and has no associated risk of induced cytotoxicity. However, UV light becomes highly attenuated as it crosses the collagen-containing tissue matrix due to its naturally wet condition, as well as by the presence of any added crosslinking agents, such as riboflavin. In other words, as the thickness of the matrix increases, the weaker the penetration of UV light into the deeper portions of the matrix. As a result, the use of UV light has so far been ineffective for crosslinking collagen-based matrices having a thickness of greater than 200 µm.

Accordingly, there exists a need for improved methods of crosslinking collagen-containing tissue matrices with UV light, particularly matrices having thicknesses of greater than 200 µm, so as to stabilize them against enzymatic degradation while also avoiding the potential biocompatibility issues associate with certain chemical crosslinkers. The present disclosure provides for such methods, as well as for crosslinked tissue matrices, and products thereof, produced by such methods.

According to various embodiments, a method for producing a crosslinked tissue matrix is provided. The method can comprise the steps of (1) dehydrating a collagen-containing tissue matrix to form a dehydrated collagen-containing tissue matrix and (2) irradiating the dehydrated collagen-containing tissue matrix with UV light such that at least a portion of the dehydrated collagen-containing tissue matrix is crosslinked. In some embodiments, the collagen-containing tissue matrix is an acellular tissue matrix. In certain embodiments, the collagen-containing tissue matrix is a dermal tissue matrix. In certain other embodiments, the collagen-containing containing tissue matrix is derived from a tissue selected from the group consisting of fascia, muscle (smooth, cardiac, or striated), pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

In some embodiments, the method further comprises impregnating the collagen-containing tissue matrix with a photo-activated crosslinker prior to step (1). In certain embodiments, the photo-activated crosslinker is riboflavin-5'-phosphate. In certain of these embodiments, the collagen-containing tissue matrix is impregnated with riboflavin-5'-phosphate by soaking it in an aqueous solution comprising riboflavin-5'-phosphate. In certain of these embodiments, the aqueous solution comprises from 0.1 to 1.0% of riboflavin-5'-phosphate. In certain of these embodiments, the aqueous solution is a phosphate-buffered saline solution. In some embodiments, the method further comprises the step of (3) rehydrating the crosslinked collagen-containing tissue matrix.

In some embodiments, the UV light is UV-A light. In certain embodiments, the UV-A light has a wavelength of approximately 370 nm.

In some embodiments, the collagen-containing tissue matrix has a thickness of greater than 200 µm. In certain embodiments, the collagen-containing tissue matrix has a thickness of 800 µm or greater.

In some embodiments, the collagen-containing tissue matrix is dehydrated via vacuum drying, air drying, or treatment with an inert gas.

In some embodiments, the entire dehydrated collagen-containing tissue matrix is irradiated with UV light. In other embodiments one or more select regions of the collagen-containing tissue matrix is irradiated with UV light. In yet other embodiments, an array of lines and/or spots on the collagen-containing tissue matrix is irradiated with UV light through a mask. In yet other embodiments, the collagen-containing tissue matrix is irradiated with UV light such that a pattern of cross-linked collagen-containing tissue matrix is obtained. In certain of these embodiments, the pattern is selected from the group consisting of serpentine patterns, web-like patterns, circular patterns, grid patterns, linear patterns, and combinations thereof.

According to other embodiments, a crosslinked tissue matrix produced by the above method is provided. In some embodiments, the crosslinked tissue matrix is in the form of a sheet.

According to other embodiments, a tissue product comprising the above crosslinked tissue matrix is provided. In some embodiments, the tissue product is a hernia repair mesh.

According to other embodiments, a tissue product comprising an acellular, collagen-containing tissue matrix is provided. The tissue matrix can be a flexible sheet having a thickness of greater than 200 µm, wherein the tissue matrix is cross-linked to a depth of greater than 200 µm from a surface of the tissue matrix, and wherein the tissue matrix is free of cytotoxic residues. In certain embodiments, the collagen-containing tissue matrix is a dermal tissue matrix. In certain other embodiments, the collagen-containing tissue matrix is derived from a tissue selected from the group consisting of fascia, muscle (striated, smooth, or cardiac), pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

In some embodiments, the tissue matrix is cross-linked across the full thickness of the tissue matrix.

In some embodiments, the collagen-containing tissue matrix has a thickness of 800 µm or greater.

In some embodiments, the collagen-containing tissue matrix is crosslinked with a photo-activated crosslinker. In certain embodiments, the photo-activated crosslinker is riboflavin-5'-phosphate.

In some embodiments, the entire collagen-containing tissue matrix is crosslinked. In other embodiments, one or more select regions of the collagen-containing tissue matrix is crosslinked. In yet other embodiments, an array of lines and/or spots on the collagen-containing tissue matrix is crosslinked. In yet other embodiments, the collagen-containing tissue matrix is crosslinked in a pattern. In certain of these embodiments, the pattern is selected from the group consisting of serpentine patterns, web-like patterns, circular patterns, grid patterns, linear patterns, and combinations thereof.

BRIEF DESCRIPTION OF THE DRAWINGS

The foregoing and other features and advantages provided by the present disclosure will be more fully understood from the following description of exemplary embodiments when read together with the accompanying drawings.

Figure 1:
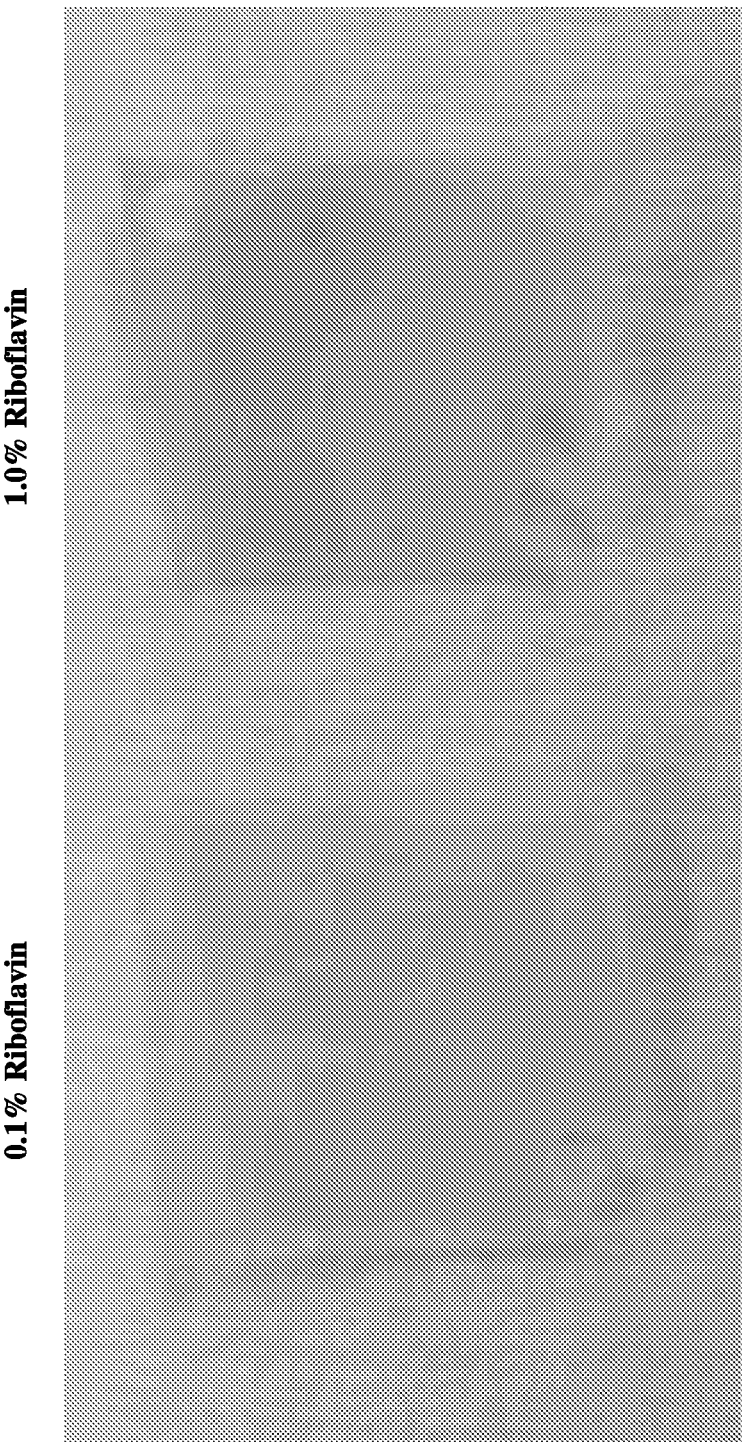
FIG. 1 depicts a photograph of collagen-based acellular dermal matrices (ADMs) after (1) treatment with 0.1% and 1% solutions of riboflavin-5'-phosphate, (2) vacuum drying, (3) 2 hours of UV-A crosslinking, and (4) rehydration in PBS buffer, according to certain embodiments.
Figure 2:
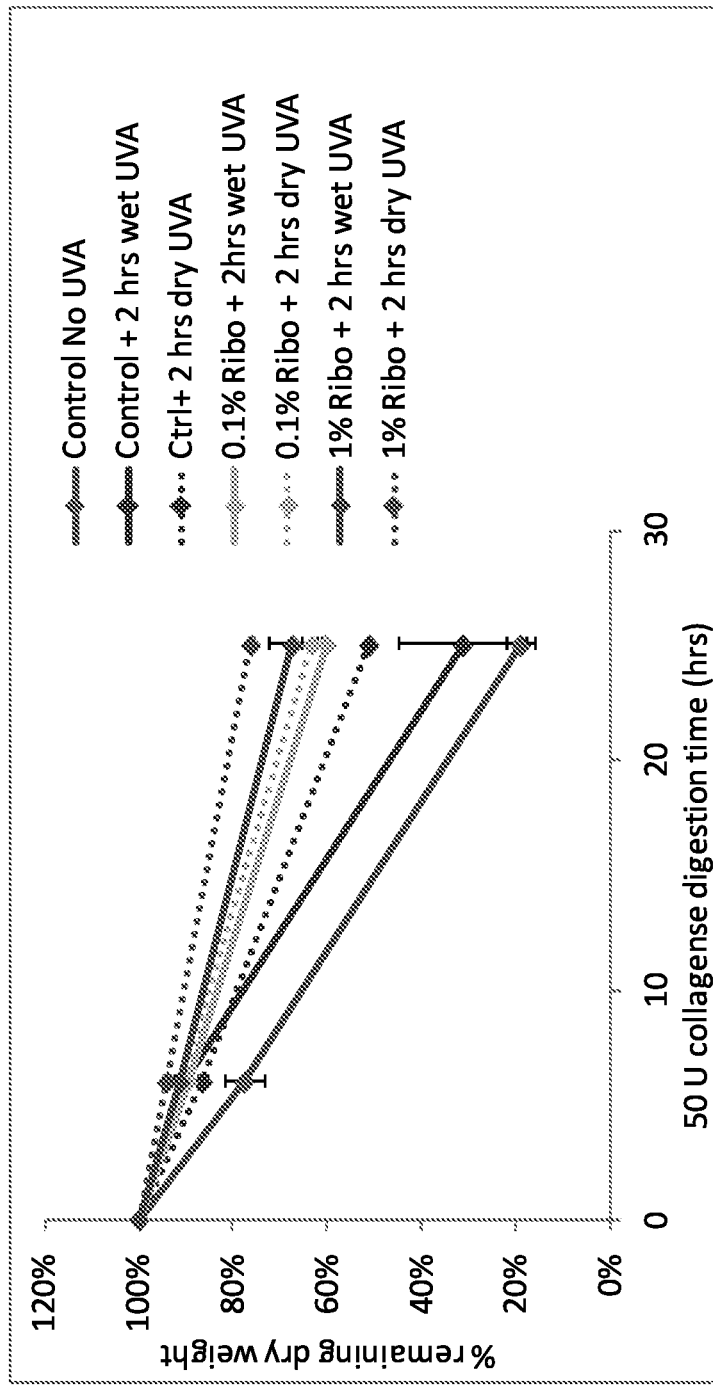
FIG. 2 graphically depicts the relative effects of wet versus dry UV-A treatments on susceptibility of the collagen-based ADMs of Examples 1, 3, and 5 and Comparative Examples 1, 3, and 5 to in vitro collagenase digestion.

DESCRIPTION OF EXEMPLARY
EMBODIMENTS

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any ranges described herein will be understood to include the endpoints and all values between the endpoints.

Any section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure provides for methods for producing a crosslinked tissue matrix. These crosslinked tissue matrices are produced by a method comprising the steps of first (1) dehydrating a collagen-containing tissue matrix to form a dehydrated collagen-containing tissue matrix and then (2) irradiating the dehydrated collagen-containing tissue matrix with UV light such that at least a portion of the dehydrated collagen-containing tissue matrix is crosslinked. Prior to the dehydration step (1), the collagen-containing tissue matrix can be impregnated with a photo-activated crosslinker. After the irradiation step (2), the crosslinked collagen-containing tissue matrix can be rehydrated with water or a pH-buffered solution, such as PBS, and subsequently sterilized. For example, the crosslinked, rehydrated collagen containing tissue matrices of the present disclosure can be sterilized by exposure to gamma radiation.

As used herein, the terms "tissue matrix" and "tissue matrices" refer to any human or animal tissue that contains extracellular matrix proteins. Examples of extracellular matrix proteins include, but are not limited to, collagens, denatured collagens, and recombinant collagens. The tissue matrices according to the present disclosure can comprise any type (i.e., Types I through XVIII) of collagen. In certain embodiments, the tissues matrices of the present disclosure comprise Type I collagen.

The tissue matrices of the present disclosure can be of any appropriate thickness, dimension, and shape for producing a tissue product useful in regenerating, repairing, augmenting, reinforcing, and/or treating human tissues. Specific examples of such thicknesses include, but are not limited to, 50 µm, 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1,000 µm, 1,500 µm, 2,000 µm, 2,500 µm, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, 25,000, 25,500, 26,000, 26,500, 27,000, 27,500, 28,000, 28,500, 29,000, 29,500, 30,000, 30,500, 31,000, 31,500, 32,000, 32,500, 33,000, 33,500, 34,000, 34,500, 35,000, 35,500, 36,000, 36,500, 37,000, 37,500, 38,000, 38,500, 39,000, 39,500, 40,000, 40,500, 41,000, 41,500, 42,000, 42,500, 43,000, 43,500, 44,000, 44,500, 45,000, 45,500, 46,000, 46,500, 47,000, 47,500, 48,000, 48,500, 49,000, 49,500, or 50,000 µm. In certain embodiments, the tissue matrices of the present disclosure are 200 µm or greater. In other embodiments, the tissue matrices of the present disclosure are 800 µm or greater. In certain embodiments, the tissue matrices of the present disclosure are in the form of a sheet.

The tissue matrices of the present disclosure may be derived from any type of tissue. Examples of the tissues that may be used to construct the tissue matrices of the present disclosure include, but are not limited to, skin, parts of skin (e.g., dermis), fascia, muscle (striated, smooth, or cardiac), pericardial tissue, dura, umbilical cord tissue, placental tissue, cardiac valve tissue, ligament tissue, tendon tissue, blood vessel tissue, such as arterial and venous tissue, cartilage, bone, neural connective tissue, urinary bladder tissue, ureter tissue, and intestinal tissue. The methods described herein can be used to crosslink any collagenous tissue type and for any tissue matrix product. For example, a number of biological scaffold materials are described by Badylak et al., and the methods of the present disclosure can be used to crosslink those or other tissue matrices known in the art. Badylak et al., "Extracellular Matrix as a Biological Scaffold Material: Structure and Function," Acta Biomaterialia (2008), doi:10.1016/j.actbio.2008.09.013.

The tissue matrices of the present disclosure include, but are not limited to, any cellularized tissue matrices, acellular tissue matrices, partially decellularized tissue matrices, decellularized tissue matrices that have been repopulated with exogenous cells (e.g., stem cells), or artificially manufactured matrices. In certain cases, decellularized products can be seeded with cells from autologous sources or other sources to facilitate treatment. As used herein, the term "acellular tissue matrix" refers generally to any tissue matrix that is substantially free of cells and/or cellular components.

The tissue matrices of the present disclosure can be selected to provide a variety of different biological and/or mechanical properties. For example, an acellular tissue matrix can be selected to allow tissue in-growth and remodeling to assist in regeneration of tissue normally found at the site where the matrix is implanted. In another example, an acellular tissue matrix, when implanted on or into fascia or other soft tissue, may be selected to allow regeneration of the fascia or other soft tissue without excessive fibrosis or scar formation. In certain embodiments, the tissue matrices of the present disclosure can be selected from ALLODERM® or STRATTICE™ (LIFECELL CORPORATION, Branchburg, N.J.), which are human and porcine acellular dermal matrices, respectively. Alternatively, other suitable acellular tissue matrices can be used, as described further below.

The tissue matrices of the present disclosure can be processed in a variety of ways to produce decellularized (i.e., acellular) or partially decellularized tissue matrices. The processing steps described below can be used along with (and either before or after) the methods described herein for producing the crosslinked tissue matrices of the present disclosure.

In general, the steps involved in the production of a partially decellularized or acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents, one or more agents to prevent crosslinking, one or more protease inhibitors, and/or one or more enzymes.

Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components). Finally, other assays that identify cell-specific components (e.g., surface antigens) can be used to determine if the tissue matrices are acellular. After the decellularization process, the tissue sample is washed thoroughly with saline.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., *J. Biol. Chem.*, 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., *Infect. Immun.*, 56: 1730 (1988); R. M. Hamadeh et al., *J. Clin. Invest.*, 89: 1223 (1992).

Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see U.S. Patent Application Pub. No. 2005/0028228 A1 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui et al., "A Porcine-Derived Acellular Dermal Scaffold that Supports Soft Tissue Regeneration: Removal of Terminal Galactose-α-(1,3)-Galactose and Retention of Matrix Structure," *Tissue Engineering*, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g., mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

The collagen-containing tissue matrices of the present disclosure can be dehydrated in any manner to form a dehydrated collagen-containing tissue matrix. Examples of suitable modes of such dehydration include, but are not limited to, vacuum drying, air drying, treatment with an inert gas, dessication by hygroscopic salts, and immersion in a strongly hygroscopic fluid, such as anhydrous alcohol or glycerol. The collagen-containing tissue matrix can be subjected to dehydration for any time period sufficient to form a dehydrated collagen-containing tissue matrix. The length of such time periods will be dependent upon factors such as the size and thickness of the collagen-containing tissue matrix, the moisture content of the collagen-containing tissue matrix, and the temperature at which the dehydration is performed. The dehydration should, at minimum, be performed at a temperature below the temperature at which collagen begins to thermally denature. Examples of such time periods include, but are not limited to, 15 minutes, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours. During dehydration, the first 90% to 95% of water content in wet tissue must be removed at a temperature below 40° C. Removal of the remaining 5% of water content can be facilitated by mild heating above 40° C. for short time periods.

In certain embodiments, the collagen-containing tissue matrices of the present disclosure can be dehydrated to specific depth of it thickness (i.e., partial thickness dehydration) and then subsequently irradiated with UV light to crosslink the dehydrated the collagen-containing tissue matrices. In particular, dehydration to a specific depth of tissue thickness can be achieved by chemical dessication. Treatment of only one side of a tissue sheet with a chemical dessicant removes moisture from the treated side of the sheet faster than it can be replenished via diffusion from the other (i.e., wet) side of the sheet. This can be done, for example, by applying glycerol to only one side of a tissue sheet. The side exposed to glycerol becomes translucent and dry, while the side exposed to water stays hydrated and opaque. This technique may be used to control or limit the effective depth of crosslinking, resulting in crosslinked collagen-containing tissue matrices according to the present disclosure having a functional gradient across their thickness or a layered or laminar structure.

As used herein, the terms "crosslinking" and "crosslinked" refer to the formation of bonds between the extracellular matrix proteins of tissue matrices of the present disclosure and to extracellular matrix proteins possessing such bonds. These bonds can be covalent bonds, electrostatic bonds (e.g., hydrogen bonds), or a combination thereof, formed between proteins of extracellular matrix. These bonds can also be the result of an atom or groups of atoms (e.g., a crosslinking agent) that is covalently or electrostatically bonded to two or more proteins of extracellular matrix.

The dehydrated collagen-containing tissue matrix of the present disclosure can be irradiated with any wavelength of UV light sufficient to crosslink at least a portion of the dehydrated collagen-containing tissue matrix. In certain embodiments, the dehydrated collagen-containing tissue matrix can be irradiated with any wavelength of UV-A light, which has a wavelength in the range of from 320 to 400 nm, UV-B light, which has a wavelength in the range of from 290 to 320 nm, UV-C light, which has a wavelength in the range of from 100 of 290 nm, or any combination thereof. Examples of UV-A light wavelengths that can be used to irradiate the dehydrated collagen-containing tissue matrix of the present disclosure include, but are not limited to, 365 and 370 nm. Examples of UV-B light wavelengths that can be used to irradiate the dehydrated collagen-containing tissue matrix of the present disclosure include, but are not limited to, 250 and 265 nm.

The dehydrated collagen-containing tissue matrix can be irradiated with UV light or, when impregnated with riboflavin-5'-phosphate as the crosslinker, electron beam radiation for any amount of time sufficient to crosslink at least a portion of the dehydrated collagen-containing tissue matrix. Examples of such time periods include, but are not limited to, 15 minutes, 30 minutes, 45 minutes, 1 hour, 2 hours, 3 hours, 4 hours, 5 hours, 6 hours, 7 hours, 8 hours, 9 hours, and 10 hours. The dehydrated collagen-containing tissue matrix can also be irradiated with UV light of any intensity sufficient to crosslink at least a portion of the dehydrated collagen-containing tissue matrix, e.g., an intensity in the range of from 1 to 100 $mW/cm^2$. Examples of such intensities include, but are not limited to, 1.0, 1.5, 2.0, 2.5, 3.0, 3.5, 4.0, 4.5, 5.0, 5.5, 6.0, 6.5, 7.0, 7.5, 8.0, 8.5, 9.0, and 10.0 $mW/cm^2$. The dehydrated collagen-containing tissue matrix can also be irradiated with any dosage of electron beam radiation sufficient to crosslink at least a portion of the dehydrated collagen-containing tissue matrix, e.g., a dosage in the range of from 12 to 22 kilograys (kGy).

In certain embodiments, the UV irradiation is performed on the dehydrated collagen-containing tissue matrix continuously until the desired degree of crosslinking is achieved. In other embodiments, the UV irradiation is performed intermittently until the desired degree of crosslinking is achieved. In certain embodiments when the dehydrated collagen-containing tissue matrix is in the form of a sheet, the tissue matrix sheet is irradiated with UV on only one side of the sheet. In other embodiments, the issue matrix sheet is irradiated with UV on both sides of the sheet.

Any source of UV light that can generate UV light at an intensity and wavelength sufficient to crosslink at least a portion of the dehydrated collagen-containing tissue matrix can be used to irradiate the dehydrated collagen-containing tissue matrix of present disclosure. Examples of such sources include, but are not limited to, short-wave UV lamps, UV gas-discharge lamps, UV light-emitting diodes (LEDs), and UV lasers. An example of an UV crosslink chamber that can be used to irradiate and crosslink the dehydrated collagen-containing tissue matrix of present disclosure is the Stratalinker 2400™ (Stratagene). As with dehydration, the temperature during UV irradiation should not exceed 40° C.

The entire dehydrated collagen-containing tissue matrix can be irradiated with UV light in accordance with the method of the present disclosure in order to crosslink at least a portion of the dehydrated collagen-containing tissue matrix. It is known that crosslinking can increase the resistance of tissue matrices to enzymatic degradation by inflammatory cells within the body and such increased resistance can slow the rate of weakening after implantation. However, excessive crosslinking can have adverse effects on cell infiltration and regeneration of normal tissue within the tissue matrix. Accordingly, in some embodiments, it may be desirable to provide localized cross-linking to the dehydrated collagen-containing tissue matrix by only irradiating one or more select regions of the dehydrated collagen-containing tissue matrix so as to maintain its ability to resist enzymatic degradation for longer times after implantation, while simultaneously providing sufficient tissue matrix mass to support normal tissue regeneration within uncrosslinked regions of the tissue matrix.

Localized crosslinking of tissue matrices may be used for a variety of other reasons. For example, it can allow production of differing strength or other mechanical properties treating the tissue to make native stronger. In addition, production of tissue matrices with localized pliability may allow a surgeon to place tissue in small openings, including passing a tissue matrix through a laparoscopic incision or trocar. Furthermore, production of tissue with localized pliability can be beneficial to allow matching of compliances with natural tissues or to match anisotropic mechanical properties of tissues.

Localized crosslinking of the dehydrated collagen-containing tissue matrices can be achieved by irradiating the tissue matrix through a mask so as to result in an array or pattern of crosslinked lines and or spots in the tissue matrix. Examples of crosslinking patterns that can obtained by irradiating only one or more select regions of the tissue matrices of the present disclosure with UV light include, but are not limited to, serpentine patterns, spiral patterns, linear patterns, curved patterns, linear or longitudinally aligned patterns, circular patterns, web-like patterns, and grid patterns.

The collagen-containing tissue matrices of the present disclosure can be impregnated with photo-activated crosslinker(s). In certain embodiments, the photo-activated crosslinker or crosslinkers are non-cytotoxic and/or do not release cytotoxic residuals upon degradation of the collagen-containing tissue matrix. Examples of such non-cytotoxic, photo-activated crosslinkers include, but are not limited to, riboflavin-5'-phosphate and salts thereof, Rose Bengal, bioflavonoids, ascorbic acid and salts thereof, and any combination thereof. Examples of specific bioflavonoids that may be used as a non-cytotoxic photo-activated crosslinker include, but are not limited to, proanthocyanidin, catechin, epicatechin, epigallo catechin, epicatechin gallate, epigallocatechin gallate, quercetin, tannic acid, and combinations thereof. Besides being a non-cytotoxic, photo-activated crosslinker, ascorbic acid and salts thereof can also act as a radioprotectant (i.e., provides protection from long term oxidative degradation via free radical scavenging). Therefore, in certain embodiments, the collagen-containing tissue matrices of the present disclosure can be impregnated with a mixture of riboflavin and ascorbic acid.

The collagen-containing tissue matrices of the present disclosure can be impregnated with the photo-activated crosslinker or crosslinkers in a number of ways. In certain embodiments, the collagen-containing tissue matrices of the present disclosure are impregnated with the photo-activated crosslinker or crosslinkers by soaking it in a solution of the photo-activated crosslinker or crosslinkers. The solvent of the solutions of photo-activated crosslinker or crosslinkers can be any suitable biocompatible solvent. An example of such biocompatible solvents includes, but is not limited to, water. The solutions of photo-activated crosslinker or crosslinkers can further comprise any suitable pharmaceutical or physiologically acceptable diluents, carriers, excipients, and/or additives. Thus, in certain embodiments the photo-activated crosslinker or crosslinkers can be formulated in pH-buffered solutions, both aqueous and non-aqueous. Examples of such pH-buffered solutions include, but is not limited to, phosphate-buffered saline (PBS) and aqueous buffering systems based on citrate, acetate, and HEPES. Furthermore, since collagen is a naturally buffered environment, in certain embodiments the photo-activated crosslinker or crosslinkers can be formulated in an unbuffered saline solution.

The photo-activated crosslinker or crosslinkers solutions with which the collagen-containing tissue matrices of the present disclosure may be impregnated can have any suitable concentration of crosslinker. The concentration can be in the range of from 0.01% to 5.0% or in the range of from 0.1% to 1.0%. Examples of specific concentrations include, but are not limited to, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, and 5.0%.

The present disclosure also provides for crosslinked tissue matrices produced by the foregoing methods. These crosslinked tissue matrices can be used to produce tissue products for treating patients. For example, various tissue products are available for regeneration, repair, augmentation, reinforcement, and/or treatment of human tissues that have been damaged or lost due to various diseases and/or structural damage (e.g., from trauma, surgery, atrophy, and/or long-term wear and degeneration). Such products can include, for example, acellular tissue matrices, tissue allografts or xenografts, and/or reconstituted tissues (i.e., at least partially decellularized tissues that have been seeded with cells to produce viable materials).

Tissue products produced from the crosslinked tissue matrices of the present disclosure may be used to repair defects (e.g., hernias), to support surrounding tissues or implants (e.g., for breast augmentation and/or reconstruction), or to replace damaged or lost tissue (e.g., after trauma or surgical resection). For example, the crosslinked tissue matrices of the present disclosure can be used to construct a hernia repair mesh, which can be used to repair abdominal wall hernias. In certain embodiments, the tissue product is a collagen sponge. In other embodiments, the tissue product is an injectable collagen formulation, such as an injectable adipose tissue matrix. Whatever the particular use, the tissue product should be sufficiently resistant to enzymatic degradation until tissue regeneration and/or repair occurs.

The tissue products of the present disclosure can also comprise an acellular, collagen-containing tissue matrix, wherein the tissue matrix is a flexible sheet having a thickness of greater than 200 µm, e.g., greater than 800 µm or at least 5,000 µm (i.e., 5 mm), wherein the tissue matrix is cross-linked to a depth of greater than 200 µm from a surface of the tissue matrix, and wherein the tissue matrix is free of cytotoxic residues, such as those that would result from the use of certain chemical crosslinkers. In certain embodiments where the tissue product is a collagen sponge, the collagen sponge can have a thickness of up to 50,000 µm (i.e., 5 cm). The tissue matrix can be crosslinked across its full thickness. The collagen-containing tissue matrix can be derived from any of the sources described above and can be crosslinked with any of the photo-activated crosslinkers described above. The entire collagen-containing tissue matrix can be crosslinked or only one or more select regions thereof, as described above.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

EXAMPLES

Example 1

A 2 cm×3 cm sample of sheet acellular dermal matrix (ADM) derived from porcine dermis and having a wet thickness of approximately 1.3 mm was vacuum dried at 35° C. at less than 100 millitorr absolute pressure for 12-24 hours, yielding a dried, semi-transparent ADM having a thickness of approximately 0.7 mm. The dried, semi-transparent ADM was then transferred to a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 2 hours. The ADM was then rehydrated overnight in Dulbecco's phosphate-buffered saline (PBS buffer) with no Ca or Mg salts (standard nominal concentration of 2.67 mM KCl, 1.47 mM KH$_2$PO$_4$, 138 mM NaCl, and 8.06 mM Na$_2$HPO$_4$.7H$_2$O).

Comparative Example 1

A 2 cm×3 cm sample of "wet" (i.e., not vacuum dried overnight) sheet acellular dermal matrix (ADM) derived from porcine dermis and having a wet thickness of approximately 1.3 mm was placed in a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 2 hours.

Example 2

A 2 cm×3 cm sample of sheet acellular dermal matrix (ADM) derived from porcine dermis and having a wet thickness of approximately 1.3 mm was vacuum dried at 35° C. at less than 100 millitorr absolute pressure for 12-24 hours, yielding a dried, semi-transparent ADM having a thickness of approximately 0.7 mm. The dried, semi-transparent ADM was then transferred to a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 4 hours. The ADM was then rehydrated overnight in Dulbecco's phosphate-buffered saline (PBS buffer) with no Ca or Mg salts (standard nominal concentration of 2.67 mM KCl, 1.47 mM KH$_2$PO$_4$, 138 mM NaCl, and 8.06 mM Na$_2$HPO$_4$.7H$_2$O).

Comparative Example 2

A 2 cm×3 cm sample of "wet" (i.e., not vacuum dried overnight) sheet acellular dermal matrix (ADM) derived from porcine dermis and having a wet thickness of approximately 1.3 mm was placed in a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 4 hours.

Example 3

A 2 cm×3 cm sample of sheet acellular dermal matrix (ADM) derived from porcine dermis and having a wet thickness of approximately 1.3 mm was soaked for up to 20 hours in a 0.1% by weight solution of riboflavin-5'-phosphate in PBS buffer (FIG. 1a). The riboflavin-treated ADM was then vacuum dried at 35° C. at less than 100 millitorr absolute pressure for 12-24 hours, yielding a dried, semi-transparent ADM (FIG. 1b) having a thickness of approximately 0.7 mm. The dried, semi-transparent ADM was then transferred to a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 2 hours (FIG. 1c). The ADM was then rehydrated overnight in Dulbecco's phosphate-buffered saline (PBS buffer) with no Ca or Mg salts (standard nominal concentration of 2.67 mM KCl, 1.47 mM KH$_2$PO$_4$, 138 mM NaCl, and 8.06 mM Na$_2$HPO$_4$.7H$_2$O) (FIG. 1d). As can be seen in FIG. 1d, the visual appearance of the crosslinked, rehydrated ADM is light yellow. This is likely caused by the presence of residual riboflavin, which can be removed with additional washing.

Comparative Example 3

A 2 cm×3 cm sample of "wet" (i.e., not vacuum dried overnight) sheet acellular dermal matrix (ADM) derived from porcine dermis and having a wet thickness of approximately 1.3 mm was soaked for up to 20 hours in a 0.1% by weight solution of riboflavin-5'-phosphate in PBS buffer. The riboflavin-treated ADM was then placed in a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 2 hours.

Example 4

A 2 cm×3 cm sample of sheet acellular dermal matrix (ADM) derived from porcine dermis and having a wet thickness of approximately 1.3 mm was soaked for up to 20 hours in a 0.1% by weight solution of riboflavin-5'-phosphate in PBS buffer. The riboflavin-treated ADM was then vacuum dried at 35° C. at less than 100 millitorr absolute pressure for 12-24 hours, yielding a dried, semi-transparent ADM having a thickness of approximately 0.7 mm. The dried, semi-transparent ADM was then transferred to a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 4 hours. The ADM was then rehydrated overnight in Dulbecco's phosphate-buffered saline (PBS buffer) with no Ca or Mg salts (standard nominal concentration of 2.67 mM KCl, 1.47 mM KH$_2$PO$_4$, 138 mM NaCl, and 8.06 mM Na$_2$HPO$_4$.7H$_2$O).

Comparative Example 4

A 2 cm×3 cm sample of "wet" (i.e., not vacuum dried overnight) sheet acellular dermal matrix (ADM) derived from porcine dermis and having a wet thickness of approximately 1.3 mm was soaked for up to 20 hours in a 0.1% by weight solution of riboflavin-5'-phosphate in PBS buffer. The riboflavin-treated ADM was then placed in a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 4 hours.

Example 5

A 2 cm×3 cm sample of sheet acellular dermal matrix (ADM) derived from porcine dermis and having a wet thickness of approximately 1.3 mm was soaked for up to 20 hours in a 1.0% by weight solution of riboflavin-5'-phosphate in PBS buffer (FIG. 1a). The riboflavin-treated ADM was then vacuum dried at 35° C. at less than 100 millitorr absolute pressure for 12-24 hours, yielding a dried, semi-transparent ADM (FIG. 1b) having a thickness of approximately 0.7 mm. The dried, semi-transparent ADM was then transferred to a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 2 hours (FIG. 1c). The ADM was then rehydrated overnight in Dulbecco's phosphate-buffered saline (PBS buffer) with no Ca or Mg salts (standard nominal concentration of 2.67 mM KCl, 1.47 mM KH$_2$PO$_4$, 138 mM NaCl, and 8.06 mM Na$_2$HPO$_4$.7H$_2$O) (FIG. 1d). As can be seen in FIG. 1d, the visual appearance of the crosslinked, rehydrated ADM is light yellow. This is likely caused by the presence of residual riboflavin, which can be removed with additional washing.

Comparative Example 5

A 2 cm×3 cm sample of "wet" (i.e., not vacuum dried overnight) sheet acellular dermal matrix (ADM) derived from porcine dermis and having a wet thickness of approximately 1.3 mm was soaked for up to 20 hours in a 1.0% by weight solution of riboflavin-5'-phosphate in PBS buffer. The riboflavin-treated ADM was then placed in a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 2 hours.

Example 6

A 2 cm×3 cm sample of sheet acellular dermal matrix (ADM) derived from porcine dermis and having a wet thickness of approximately 1.3 mm was soaked for up to 20 hours in a 1.0% by weight solution of riboflavin-5'-phosphate in PBS buffer. The riboflavin-treated ADM was then vacuum dried at 35° C. at less than 100 millitorr absolute pressure for 12-24 hours, yielding a dried, semi-transparent ADM having a thickness of approximately 0.7 mm. The dried, semi-transparent ADM was then transferred to a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 4 hours. The ADM was then rehydrated overnight in Dulbecco's phosphate-buffered saline (PBS buffer) with no Ca or Mg salts (standard nominal concentration of 2.67 mM KCl, 1.47 mM KH$_2$PO$_4$, 138 mM NaCl, and 8.06 mM Na$_2$HPO$_4$.7H$_2$O).

Comparative Example 6

A 2 cm×3 cm sample of "wet" (i.e., not vacuum dried overnight) sheet acellular dermal matrix (ADM) derived from porcine dermis and having a wet thickness of approximately 1.3 mm was soaked for up to 20 hours in a 1.0% by weight solution of riboflavin-5'-phosphate in PBS buffer. The riboflavin-treated ADM was then placed in a UVP model CL-1000 ultraviolet crosslinker using UVA lamps emitting a UV wavelength in the range of from 350-375 nm (target 365 nm) and irradiated with 370 nm wavelength UV-A light at an intensity of 5.5 mW/cm$^2$ for 4 hours.

Control Example

"Wet" (i.e., not vacuum dried overnight) sheet ADM that was neither soaked in a solution of riboflavin-5'-phosphate nor irradiated with UV-A light was used as the control.

The ADMs produced in the above Examples were tested according to the following protocols without terminal sterilization.

Differential Scanning Calorimetry (DSC)

Examples 1-6, Comparative Examples 1-6, and the Control Example were each analyzed by DSC to determine the effect that drying the samples prior to UV irradiation has on the thermal denaturation of the ADMs. A higher onset temperature of collagen thermal denaturation was observed for Examples 1-6 (dried samples prior to UV irradiation) compared to each of their respective counterparts of Comparative Examples 1-6. The higher thermal onset temperatures for the dried samples indicates a lack of denaturation compared to samples that were irradiated when fully hydrated.

In Vitro Collagenase Digestion

Examples 1, 3, and 5, Comparative Examples 1, 3, and 5, and the Control Example were each subjected to in vitro collagenase digestion to determine the effect drying prior to UV irradiation has on the degree to which collagenase digests the collagen of the ADMs over a given time period. A higher degree of collagenase resistance (as measured by % retention of dry weight) was observed for Examples 1, 3, and 5 compared to each of their respective counterparts Comparative Examples 1, 3, and 5. FIG. 3 illustrates the improved resistance of ADMs dried prior to UVA treatments to in vitro collagenase degradation.

What is claimed is:

1. A method for producing a crosslinked tissue matrix, comprising:
    (1) dehydrating a collagen-containing tissue matrix to form a dehydrated collagen-containing tissue matrix, wherein the collagen-containing tissue matrix is a dermal tissue matrix and has a thickness of greater than 200 µm; followed by
    (2) irradiating the dehydrated collagen-containing tissue matrix with UV light such that at least a portion of the dehydrated collagen-containing tissue matrix is crosslinked and such that the crosslinked tissue matrix is free of cytotoxic residues.

2. The method of claim 1, wherein, prior to step (1), the collagen-containing tissue matrix is impregnated with a photo-activated crosslinker and wherein the photo-activated crosslinker is riboflavin-5'-phosphate.

3. The method of claim 1, wherein the collagen-containing tissue matrix is impregnated with riboflavin-5'-phosphate by soaking it in an aqueous solution comprising riboflavin-5'-phosphate.

4. The method of claim 3, wherein the aqueous solution comprises from 0.1 to 1.0% by weight of riboflavin-5'-phosphate and wherein the aqueous solution is a phosphate-buffered saline solution.

5. The method of claim 1, wherein the UV light is UV-A light that has a wavelength of 370 nm.

6. The method of claim 1, wherein the collagen-containing tissue matrix is dehydrated via vacuum drying, air drying, or treatment with an inert gas.

7. The method of claim 1, further comprising:
   (3) rehydrating the crosslinked collagen-containing tissue matrix.

8. The method of claim 1, wherein the entire dehydrated collagen-containing tissue matrix is irradiated with UV light; or wherein one or more select regions of the collagen-containing tissue matrix is irradiated with UV light; or wherein an array of lines and/or spots on the collagen-containing tissue matrix is irradiated with UV light through a mask.

9. The method of claim 1, wherein the collagen-containing tissue matrix is irradiated with UV light such that a pattern of cross-linked collagen-containing tissue matrix is obtained.

\* \* \* \* \*